(12) United States Patent
Xu et al.

(10) Patent No.: US 11,903,418 B2
(45) Date of Patent: Feb. 20, 2024

(54) COMPOSITE MICRO-VAPORIZER WICKS

(71) Applicant: Blackship Technologies Development LLC, North Chesterfield, VA (US)

(72) Inventors: Yongjie Xu, Richmond, VA (US); Donovan Phillips, Richmond, VA (US)

(73) Assignee: Blackship Technologies Development LLC, North Chesterfield, VA (US)

( * ) Notice: Subject to any disclaimer, the term of this patent is extended or adjusted under 35 U.S.C. 154(b) by 354 days.

(21) Appl. No.: 17/029,817

(22) Filed: Sep. 23, 2020

(65) Prior Publication Data
US 2021/0001058 A1 Jan. 7, 2021

Related U.S. Application Data

(63) Continuation of application No. 15/639,139, filed on Jun. 30, 2017, now Pat. No. 10,792,443.

(51) Int. Cl.
*A24F 40/44* (2020.01)
*A24F 40/20* (2020.01)
(Continued)

(52) U.S. Cl.
CPC ........... *A24F 40/44* (2020.01); *A61M 11/044* (2014.02); *H05B 3/44* (2013.01); *A24F 40/10* (2020.01);
(Continued)

(58) Field of Classification Search
CPC .......... A24F 40/44; A24F 40/40; A24F 40/10; A24F 47/008
See application file for complete search history.

(56) References Cited

U.S. PATENT DOCUMENTS

| 4,800,903 A | 1/1989 | Ray et al. |
| 9,549,573 B2 | 1/2017 | Monsees et al. |

(Continued)

FOREIGN PATENT DOCUMENTS

| CN | 1196660 A | 10/1998 |
| CN | 101843368 A | 9/2010 |

(Continued)

OTHER PUBLICATIONS

Mathopenref.com "Cylinder", pulled from https://www.mathopenref.com/cylinder.html on Sep. 10, 2022. published 2011 (Year: 2011).*

(Continued)

*Primary Examiner* — Alex B Efta
(74) *Attorney, Agent, or Firm* — Nixon & Vanderhye P.C.

(57) ABSTRACT

A composite wick is provided for use in a micro-vaporizer having a fluid reservoir and a heating element. The composite wick comprises a wick body positionable so that its upstream surface is in fluid communication with the fluid reservoir and the downstream surface is disposed in opposition to a surface of the heating element. The wick body comprises at least one base wick structure having a plurality of tortuous passages that collectively provide a capillary effect to draw fluid from the reservoir and transport it toward the downstream surface. The wick body further comprises an active material positioned within the wick body so that vaporizable fluid drawn through the wick body contacts and interacts with the active material. The active material is selected to impart a desired characteristic to the vaporizable fluid.

26 Claims, 13 Drawing Sheets

(51) Int. Cl.
*A24F 40/10* (2020.01)
*A61M 11/04* (2006.01)
*H05B 3/44* (2006.01)
*A61M 15/06* (2006.01)

(52) U.S. Cl.
CPC .............. *A24F 40/20* (2020.01); *A61M 15/06* (2013.01); *H05B 2203/021* (2013.01)

(56) References Cited

U.S. PATENT DOCUMENTS

| | | | |
|---|---|---|---|
| 9,642,397 | B2 | 5/2017 | Dai et al. |
| 10,792,443 | B2* | 10/2020 | Xu .......................... H05B 3/44 |
| 2008/0092912 | A1 | 4/2008 | Robinson et al. |
| 2011/0155153 | A1* | 6/2011 | Thorens ................. A24F 40/46 131/329 |
| 2011/0309157 | A1* | 12/2011 | Yang ................. A61M 15/0021 239/6 |
| 2014/0069424 | A1 | 3/2014 | Poston et al. |
| 2014/0096872 | A1* | 4/2014 | Yoshioka ........... B23K 35/0244 148/528 |
| 2014/0123989 | A1* | 5/2014 | LaMothe .......... A61M 15/0003 131/328 |
| 2014/0166029 | A1* | 6/2014 | Weigensberg .......... A24F 40/30 131/329 |
| 2014/0261487 | A1 | 9/2014 | Chapman |
| 2015/0068541 | A1 | 3/2015 | Sears et al. |
| 2015/0196057 | A1 | 7/2015 | Wu |
| 2015/0196058 | A1 | 7/2015 | Lord |
| 2015/0245669 | A1 | 9/2015 | Cadieux |
| 2016/0331028 | A1 | 11/2016 | Xu |
| 2017/0020190 | A1 | 1/2017 | Chang |
| 2017/0325506 | A1* | 11/2017 | Batista ................. A24F 40/465 |
| 2018/0140014 | A1* | 5/2018 | Yu ........................... H05B 3/06 |

FOREIGN PATENT DOCUMENTS

| | | | |
|---|---|---|---|
| CN | 204426696 | U | 7/2015 |
| CN | 104853632 | A | 8/2015 |
| CN | 106136333 | A | 11/2016 |
| CN | 106418715 | A | 2/2017 |
| CN | 106455712 | A | 2/2017 |
| CN | 206025215 | U | 3/2017 |
| CN | 206079033 | U | 4/2017 |
| CN | 106659250 | A | 5/2017 |
| CN | 106659274 | A | 5/2017 |
| CN | 206165813 | U | 5/2017 |
| CN | 110113959 | A | 8/2019 |
| JP | 2010506594 | | 3/2010 |
| JP | 2017506915 | | 3/2017 |
| JP | 2017507647 | | 3/2017 |
| WO | 2015177043 | A1 | 11/2015 |
| WO | 2016135342 | A2 | 9/2016 |
| WO | WO 2018122978 | | 7/2018 |
| WO | WO-2018122978 | A1 * | 7/2018 ........... A24B 15/167 |

OTHER PUBLICATIONS

National Intellectual Property Administration, PRC, Chinese Patent Application No. 201810687533.X, Notification of Second Office Action, dated Jun. 15, 2021, pp. 1-25 (English Translation).

State Intellectual Property Office of PRC, Chinese Patent Application No. 201810687533.X, Notification of First Office Action, dated Sep. 24, 2020, pp. 1-28 (English Translation).

Kominami et al., "JP 2018122978 A1, machine translation" published Jul. 5, 2018 (Year: 2018).

European Patent Office, Communication including Extended European Search Report, European Patent Application No. 18179610.3, pp. 1-8, dated Oct. 10, 2018.

Japanese Intellectual Property Office, Japanese Patent Application No. 2018-109956, Decision to Grant Patent, dated Jul. 7, 2022, pp. 1-4 (Includes English Abstract).

* cited by examiner

COMPOSITE MICRO-VAPORIZER WICKS

This application is a continuation of U.S. application Ser. No. 15/639,139, filed Jun. 30, 2017, the complete disclosure of which is incorporated herein by reference.

BACKGROUND OF THE INVENTION

The invention relates generally to micro-vaporizer wicking materials and, more particularly, to composite micro-vaporizer wicks formed from a fiber material and an active flavor material.

Micro-vaporizers are devices in which a vaporizable fluid is drawn from a storage reservoir into a chamber where it is heated to vaporization temperature by a heating element. The vaporized fluid is then drawn or forced from the chamber. In products such as electronic cigarettes (also known as e-cigarettes or personal vaporizers), the vaporized fluid is drawn from the chamber through a mouthpiece and inhaled by the user. In other products the vaporized fluid is dispersed into the atmosphere.

The usual purpose of a device that uses a micro-vaporizer is to dispense one or more active substances using the vaporized fluid. In atmospheric dispensers, these substances may include materials such as deodorizing agents, fragrance, and insect repellant. In the case of personal vaporizers, the active substances typically include a flavorant (i.e., a flavoring agent or material) and nicotine. The flavorant and nicotine levels may be selected so as to mimic the experience of smoking a cigarette. In general, the vaporizable fluid is the sole source of active substances exiting the micro-vaporizer.

SUMMARY OF THE INVENTION

An illustrative aspect of the invention provides a composite wick for use in a micro-vaporizer. The micro-vaporizer has a micro-vaporizer body in which is disposed a vaporizable fluid reservoir and a vaporization chamber with a heating element at least partially disposed therein. The composite wick comprises a wick body having an upstream surface and a downstream surface. The wick body is positionable within the micro-vaporizer body so that the upstream surface is in fluid communication with the vaporizable fluid reservoir and the downstream surface is disposed within the vaporization chamber in opposition to a surface of the heating element. The wick body comprises at least one base wick structure having a plurality of tortuous passages that collectively provide a capillary effect to draw vaporizable fluid from the vaporizable fluid reservoir and transport it toward the downstream surface. The wick body further comprises an active material positioned so that vaporizable fluid drawn through the wick body contacts and interacts with the active material. The active material is selected to impart a desired characteristic to the vaporizable fluid.

In another illustrative aspect of the invention provides a method of modifying vaporization products produced in a micro-vaporizer. The micro-vaporizer has a micro-vaporizer body in which is disposed a vaporizable fluid reservoir and a vaporization chamber with a selectively activated heating element at least partially disposed therein. The method comprises positioning a composite wick intermediate the vaporizable fluid reservoir and the heating element for transporting vaporizable fluid therebetween. The composite wick comprises a base wick structure configured to draw vaporizable fluid toward the downstream surface of the wick and an active material selected to impart a desired charac- teristic to the vaporizable fluid. The method further comprises allowing vaporizable fluid to flow from the reservoir into and through the composite wick, thereby causing the vaporizable fluid to interact with the active material to produce a modified vaporizable fluid mixture. The method also comprises activating the heating element to vaporize the modified vaporizable fluid mixture at or near the downstream surface of the wick, thereby producing modified vaporization products.

BRIEF DESCRIPTION OF THE DRAWINGS

The invention can be more fully understood by reading the following detailed description together with the accompanying drawing, in which like reference indicators are used to designate like elements, and in which.

DETAILED DESCRIPTION OF THE INVENTION

While some micro-vaporizers use other mechanisms for transport of the vaporizable fluid from a reservoir to a vaporization chamber, most use some form of wick or fibrous wicking materials. In general, the wicking materials are selected based on their wicking properties (capillarity, porosity, hydrophilicity, surface energy, etc.), compatibility with the vaporizable fluid, and heat tolerance. In most cases, these materials are also likely to be selected so that they do not themselves contribute to the material exiting the vaporization chamber. In personal vaporizers, for example, wicking materials are chosen to impart as little or no flavor as possible.

The present invention provides composite micro-vaporizer wicks and wicking materials that provide, not only the requisite properties for transporting the vaporizable fluid, but also a mechanism for supplementing the active substances in the vaporized fluid. As will be discussed in more detail hereafter, the composite wick materials of the invention may be in the form of woven or non-woven fibrous materials in combination with embedded, trapped, adhered or alternately layered active additive materials. They are generally configured so that, in transport from the fluid reservoir to the vaporization chamber and/or heating element, the vaporizable fluid must come into contact with the active additive materials. Portions of the active additive materials may be released into the fluid or may otherwise affect or impart desired characteristics to the fluid.

The invention will be described in more detail using examples and embodiments geared primarily to personal vaporizers. It will be understood, however, that the methods of the invention are not limited to such applications and can be applied to any micro-vaporizer device.

Figure 1:
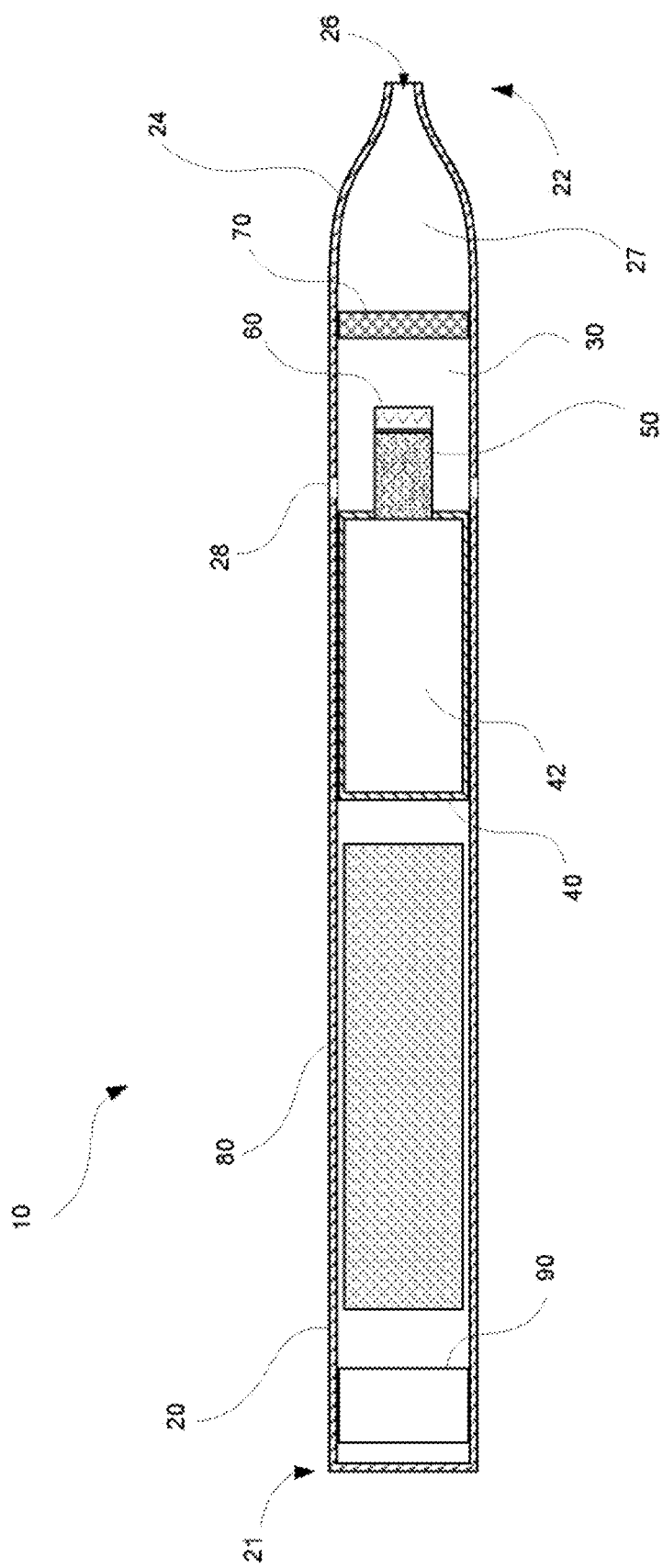
FIG. 1 is a cross-sectional view of a personal vaporizer usable in conjunction with embodiments of the invention.

With reference to FIG. 1, a typical personal vaporizer 10 comprises a cylindrical casing 20 having a distal end 21 and a proximal end 22. At its proximal end 22, the casing 20 is formed into a mouthpiece 24 having a passage 26 providing fluid communication between the atmosphere and an exit chamber 27 inside the casing 20. The casing 20 also has one or more air holes 28 to allow air to flow from the atmosphere into a vaporization chamber 30 inside the casing 20 when a relative vacuum is applied at the mouthpiece passage 26 (e.g., by inhalation of a device user). The air drawn in through the air hole(s) 28 passes through a filter 70 which divides the vaporization chamber 30 and the exit chamber 27.

The personal vaporizer 10 further comprises a fluid reservoir 40 in which is disposed a vaporizable fluid 42. The fluid reservoir 40 may be configured as a simple tank in which the fluid 42 is disposed. In some embodiments, the reservoir 40 may be or include a housed or unhoused adsorptive or absorptive material or structure that retains the vaporizable fluid 42. A fluid transport structure 50 is configured and positioned to be in contact with the fluid 42 in the reservoir 40 and for drawing the fluid 42 out of the reservoir 40 and into the vaporization chamber 30. The fluid transport structure 50 may be further configured for bringing the drawn fluid 42 into close proximity or in contact with a heating element 60. The heating element 60 may be configured to heat the vaporizable fluid through any conductive, convective, and/or radiative heat transfer mechanism. In typical vaporizers, the heating element 60 is or includes a resistance element in the form of a wire coil. In some cases, the resistance element is housed within a heat conductive casing.

The illustrative personal vaporizer 10 also comprises a battery 80 for powering the heating element and a control unit 90. It will be understood that the configuration and relative positioning of the components of the personal vaporizer 10 may be widely varying and that additional components (e.g., an airflow controller for regulation of the amount of air flow through the holes 28) may be included.

To use the personal vaporizer 10, a user activates the heating element 60 and draws air through the device by inhaling through the mouthpiece. The vaporizable fluid 42 in the chamber 30 is heated to its vaporization point by the heating element 60. The resulting vapor mixes with air drawn through the air holes 28 and the mixture is drawn through the filter 70 and the exit chamber 27 and out through the mouthpiece passage 26.

The fluid transport structure 50 of the personal vaporizer 10 may be or comprise a wick or collection of wicking material. Typical personal vaporizer wicks are formed from organic fiber materials such as cotton, jute, flax, cellulose, or hemp. Some non-organic materials such as silica, carbon, and non-organic polymer fibers, ceramics and steel mesh may also be used. In general, vaporizer wicks can be formed from any material that is thermally stable and that provides sufficient wicking action to transport the vaporizable fluid 42 from the reservoir 40 to the heating element 60.

The composite wicks of the present invention are configured to provide stable, consistent wicking characteristics, but also provide the benefits of including one or more active materials that come into contact with the fluid prior to and/or during vaporization. As used herein, the term "active material" refers to any material that controllably alters or adds to the vaporization products of the device. Depending on the application, active materials can include, without limitation, plant material, minerals, deodorizing agents, fragrances, insect repellants, medications, and disinfectants and any material or structure containing or incorporating any of the foregoing.

In the specific instance of personal vaporizers, active materials may include flavorant substances that augment the flavorant of the vaporizable fluid. These may include, without limitation, marijuana, hemp, cannabidiol (cbd), citronella, geraniol, mint, thyme, tobacco, *Salvia dorrii, salvia, Passiflora incarnata, Arctostaphylos uva-ursi, Lobelia inflata*, lemon grass, cedar wood, clove, cinnamon, coumarin, helio, vanilla, menthol, *eucalyptus*, peppermint, rosemary, lavender, licorice, and cocoa and any material or structure containing or incorporating any of the foregoing. One active material of particular interest for personal vaporizers is tobacco, which can be provided in the form of whole tobacco leaves, shredded tobacco leaves, crushed and dried tobacco flakes, slivers of dried tobacco leaves, and shavings from dried tobacco leaves. In some embodiments, it may be incorporated into woven or a non-woven fiber sheet with tobacco material weaved or embedded into the non-woven fiber sheet.

In some cases, active materials may be selected based on their tendency to release flavoring or other agents upon heating. Some materials may, for example, begin to decompose or off-gas upon reaching a certain temperature. For any particular such active material, the temperature at which the material begins to decompose or off-gas is referred to herein as the material's release temperature. For a combustible active material, temperatures falling between the material's release temperature and its combustion temperature are referred to herein as being in the material's release temperature range.

The following paragraphs describe composite wicks according to various embodiments of the invention.

Figure 2:
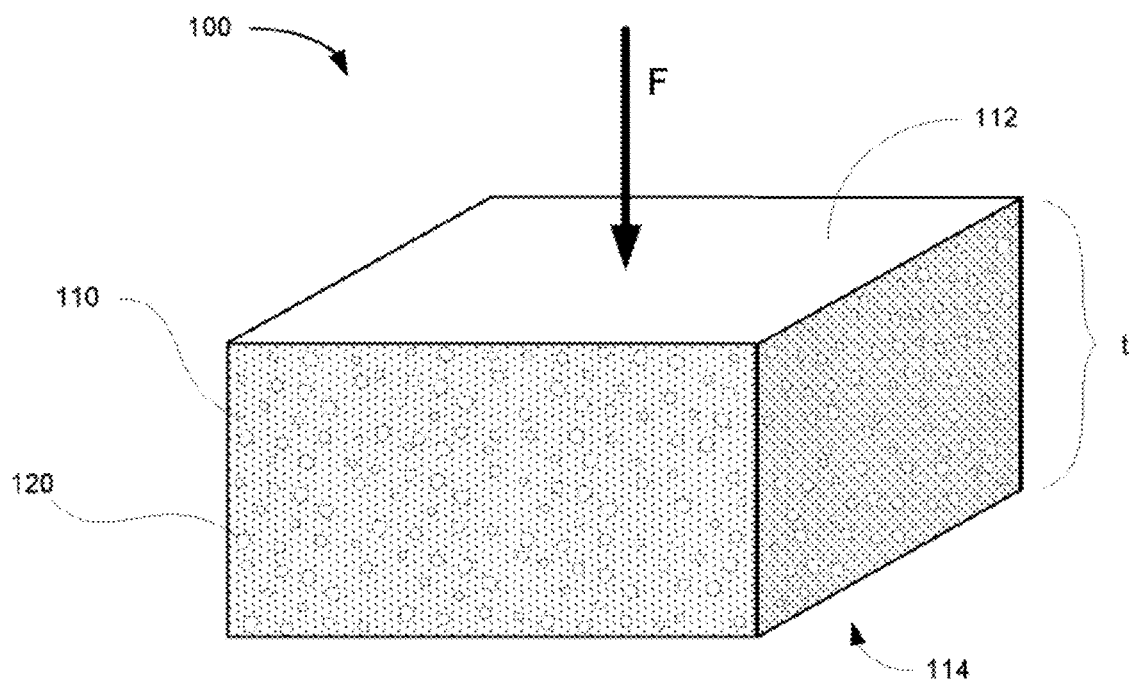
FIG. 2 is a perspective view of a composite wick according to an embodiment of the invention.

With reference to FIG. 2, a composite wick 100 according to an embodiment of the invention includes a base wick structure 110 and an inter-dispersed active material 120. The base wick structure 110 has an upstream surface 112 through which fluid is drawn into the wick 100 and a downstream surface 114. The primary flow direction through the wick 100 is designated by the arrow F. The distance between the upstream surface 112 and the downstream surface 114 defines a generally uniform thickness t. The downstream surface 114 will generally be oriented toward (i.e., facing) or in contact with a heating element to vaporize fluid at or near the downstream surface 114 or after the fluid has passed through the downstream surface 114.

The base wick structure may be formed from any of the wicking materials disclosed herein. In preferred embodiments, the base wick structure 110 is formed from organic or inorganic hydrophilic fibers. The particular fiber materials used may be selected according to the desired wicking and flow characteristics, compatibility with the vaporizable fluid and the active materials, and heat tolerance. In some cases, fibers can be coated with materials that increase hydrophilicity and/or surface energy to enhance the wicking action of the fiber. Wicking can also be optimized based on fiber size and type (e.g., stranded versus staple fibers).

In some applications, the wick material may also be selected, in part, based on its absorption and/or fluid retention characteristics. For example, the wick material may be selected to provide a particular range of saturation. In particular embodiments, the wick material of some or all of the base wick structure 110 may be configured specifically to optimize fluid retention. In such embodiments, the base wick structure may itself act as a reservoir for the vaporizable fluid. In this capacity, the base wick structure 110 may supplement or replace the separate micro-vaporizer reservoir. In micro-vaporizers having a fluid reservoir that is or includes an absorptive structure, the base wick structure 110 may be bonded to or integrally formed with the absorptive structure of the reservoir.

The wick material may also be selected based on the degree to which it expands upon contact with liquid. This can be used, inter alia, to provide a seal against liquid leakage and/or the passage of air through the wick structure.

The wick fibers may be woven or bonded to form a self-sustaining structure. In a particular embodiment, the wick structure 110 is a self-sustaining structure in which the fibers are thermally or chemically bonded to one another at spaced apart points of contact. Alternatively, the wick structure 110 may be formed as an unbonded, non-woven web. Such a web may be compressed or mechanically entangled (e.g., by needle punching) to impart a degree of structural integrity. Alternatively or in addition, structural integrity of the non-woven web may be maintained by enclosing the web in a casing or membrane or by bounding the web by other structural materials.

In all embodiments, the base wick structure 110 is formed with tortuous, interstitial passages that provide the desired capillarity and porosity characteristics of the wick. The structure of these passages can be tailored through material selection (e.g., fiber material, size, type, surface treatment, etc.) and selection of manufacturing methodology and process parameters. Flow characteristics may also be tailored through the use of fiber orientation. The flow characteristics of the base wick structure 110 may be tailored to provide optimum fluid flow rates. Such flow rates may be established based, not only on a desired vaporization rate, but on the desire to use the fluid to keep temperatures in the base wick structure 110 and the active material 120 within acceptable ranges. In some embodiments, for example, it may be desirable to tailor fluid flow so as to maintain the temperature of some or all of an active material within its release temperature range. In other embodiments, it may be desirable to tailor the fluid flow so that a limited, controlled amount of the active material exceeds its combustion temperature.

The active material 120 may be provided in any form that can be entrapped within or adjacent the interstitial passages of the base wick structure. Alternatively, the active material may be bonded to the base wick structure 110 that defines the interstitial passages. In various embodiments, the active material 120 can be provided in the form of powder, larger particles, or flakes. In embodiments in which the base wick structure 110 is formed from fiber materials, the active material 120 may be bonded to the fibers before or after formation of the base wick structure from the fibers. The active material 120 can be distributed randomly throughout the base wick structure 110 or can be preferentially distributed toward particular regions (e.g., with a higher density adjacent the upstream surface 112 or the downstream surface 114). As will be discussed in more detail below, the active material 120 may be disposed so that a portion of the material is exposed at one or both of the upstream and downstream surfaces 112, 114.

When placed in a micro-vaporizer device such as the personal vaporizer 10, the composite wick 100 is positioned so that the upstream surface 112 is in contact with the vaporizable fluid in or from a reservoir and the downstream surface 114 is adjacent or in contact with the heating element. The vaporizable fluid is drawn into and through the wick in flow direction F. As it passes through the wick, the fluid encounters and interacts with the active material 120 so that the nature and/or constitution of the fluid is changed. In particular embodiments, portions of the active material 120 may be dissolved in the fluid. In others, detached particles of the active material 120 may be suspended within the fluid. These particles may be small enough to pass through the tortuous passages in the wick structure 110 with the fluid. In some embodiments, flavoring material or other agents may be released into the vaporizable fluid as the result of the active material 120 being above its release temperature.

When the heating element of the micro-vaporizer device is activated, the fluid at or near the downstream surface 114 of the wick 100 is heated. Depending on the thermal output of the heating element, its proximity to the downstream surface 114 and the thermal characteristics of the base wick structure 110, the vaporizable fluid (as altered by the active material 120) may begin to vaporize within the base wick structure 110 so that the fluid exiting the wick is in vapor form or is a combination of liquid and vapor. Any fluid not vaporized within the wick 100 is vaporized after exiting the wick 100.

In addition to heating the vaporizable fluid, the heating element will also heat any portions of the base wick structure 110 and the active material 120 that are exposed at the downstream surface 114. Heat absorbed at the downstream surface 114 will also be conducted into the wick 100 establishing a temperature gradient therein. The vaporizable fluid flowing through the base wick structure 110, however, will absorb and carry away much of the heat taken in at the downstream surface 114. As noted, above, the flow characteristics of the base wick structure 110 can be tailored to provide a desired degree of cooling and, thus, a desired temperature gradient through the wick 100. This allows, for example, the ability to keep the temperature of the base wick structure 110 below material degradation temperatures. It also allows the ability to maintain at least some of the active material 120 within a desired temperature range (e.g., its release temperature range).

In some instances, the active material 120 used in the composite wick 100 may be provided in a form that has one or more dimensions that are larger than the remaining dimension(s). In such instances, the active material 120 may be positioned so as to have a particular orientation relative to the primary flow direction F through the wick structure 110. FIG. 3 illustrates a composite wick 100' that is a particular variation of the composite wick 100 in which the active material 120' is provided in the form of roughly planar flakes. As shown in FIG. 2, these flakes are positioned within the base wick structure 110 in such a manner so as to be roughly orthogonal to the primary flow direction F. In some embodiments, the active material 120' may be porous so that when positioned orthogonal to the flow direction F, the wicked fluid may pass through as well as around the flakes of active material 120', thereby increasing contact between the fluid and the active material 120'.

In some applications, it may be desirable for a portion of the active material to be exposed as the surface of one or both of the upstream and downstream surfaces 112, 114 of the composite wick 100. This provides direct exposure of some of the active material 120 to the heating element, which may be advantageous in terms of heating that portion of material above its release temperature. One example of this is where the active material in a personal vaporizer wick is tobacco. Heretofore, efforts to mimic the smoky, burning flavor of a cigarette or cigar in personal vaporizers have been largely unsuccessful. It has been found, however, that in certain embodiments of the composite wicks of the invention, tobacco materials can be disposed so that a portion of the tobacco is directly exposed to the heating element of the micro-vaporizer. This direct exposure results in the tobacco material being heated above its release temperature, which results in additional particles and/or gas products entering the vapor/air mixture in the vaporization chamber. As previously described, the flow characteristics of the base wick structure 110 can be tailored to assure that the fluid flowing around the tobacco material cools it enough to prevent the tobacco material from reaching its combustion temperature (i.e., to keep it from actually burning). In some cases, it may actually be desirable for a small amount of the tobacco to burn. In such cases, the base wick structure 110 can be tailored so that a controlled amount of the tobacco material reaches or exceeds its combustion temperature.

Figure 3:
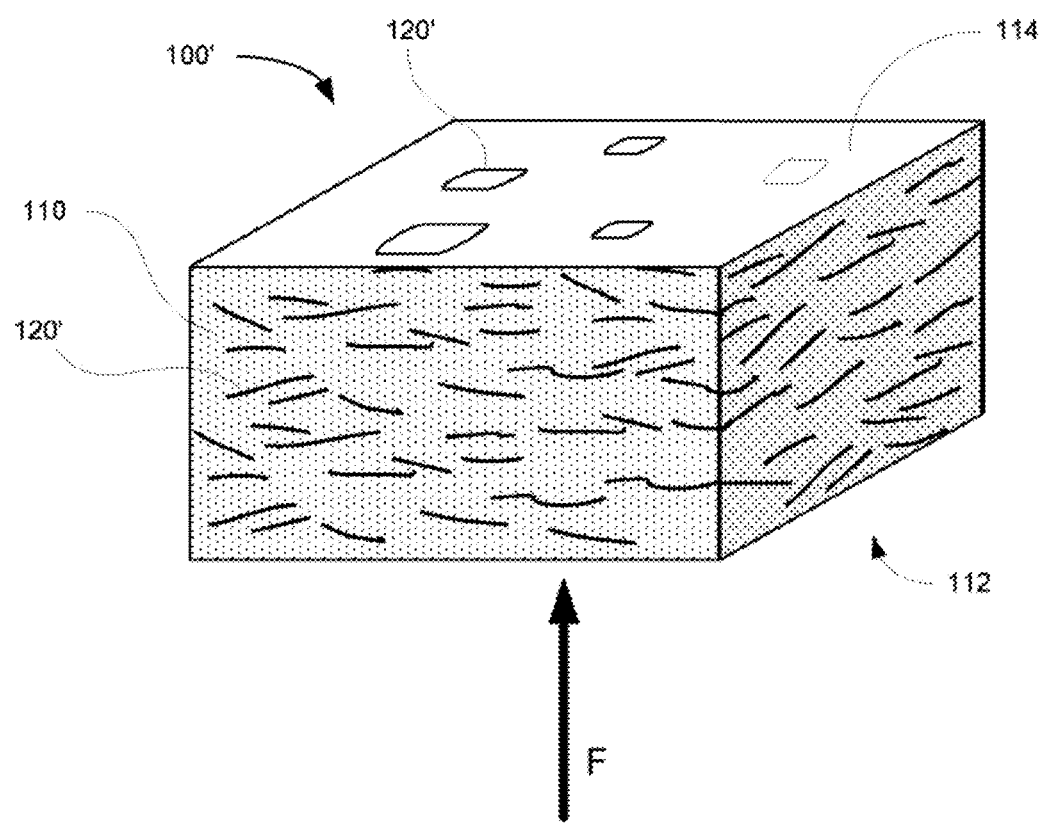
FIG. 3 is a perspective view of a composite wick according to an embodiment of the invention.

In the composite wick 100' of FIG. 3, it can be seen that the flake-like active material 120' (which could be, for example, tobacco flakes) is distributed in the base wick structure 110 in such a way that portions of some flakes are exposed at the downstream surface 114. These flakes are still held in place by the base wick structure 110, but will be directly exposed to the heating element when the wick 100 is positioned in the micro-vaporizer.

Figure 4:
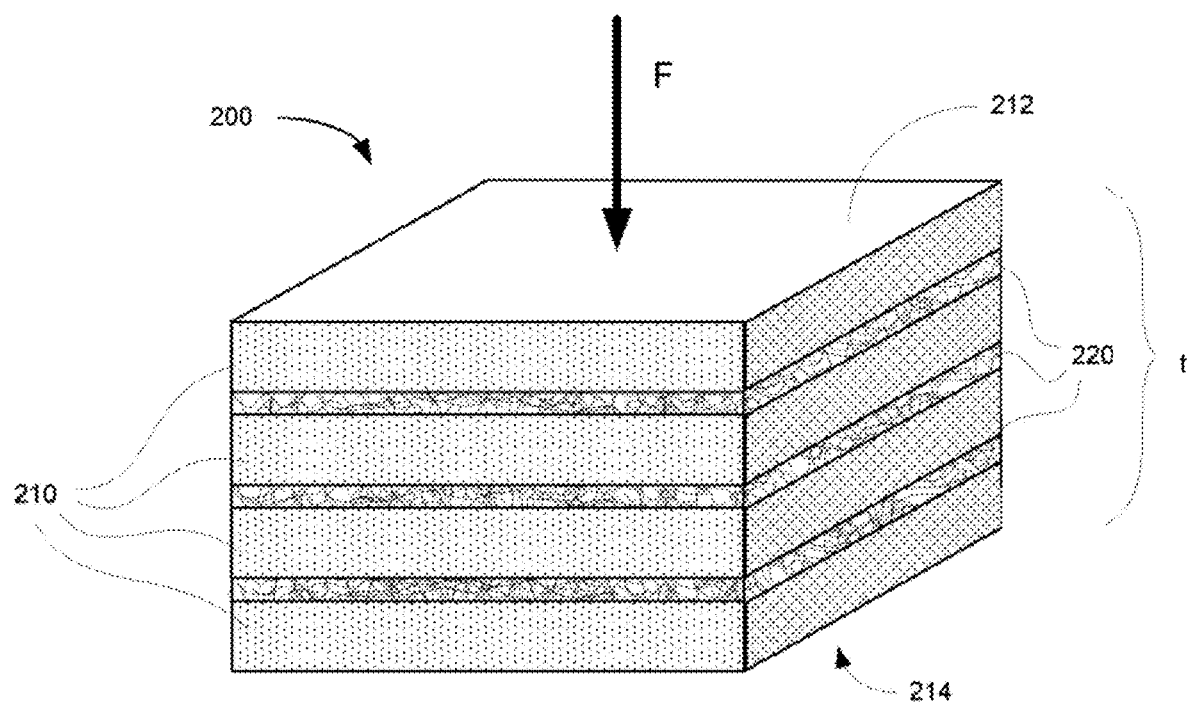
FIG. 4 is a perspective view of a composite wick according to an embodiment of the invention.

FIG. 4 illustrates a composite wick 200 according to another embodiment of the invention. The composite wick 200 is a layered structure that includes two or more base wick layers 210 alternating with one or more active material layers 220. The outermost base wick layers 210 define an upstream surface 212 through which fluid is drawn into the wick 200 and a downstream surface 214. The primary flow direction through the wick 200 is again designated by the arrow F. The distance between the upstream surface 212 and the downstream surface 214 defines a generally uniform thickness t. The downstream surface 214 will generally be oriented toward or in contact with a heating element to vaporize fluid at or near the downstream surface 214 or after the fluid has passed through the downstream surface 214. The base wick layers 210 may be formed from the same materials and have substantially the same structure as the base wick structure 110 of the composite wick 100. Thus, each base wick layer 210 is formed with tortuous, interstitial passages that provide the desired capillarity and porosity characteristics of the wick. It will be understood, however, that the characteristics of the layers 210 need not be the same. For example, different layers may have different thicknesses and/or flow-through or wicking properties. In some embodiments, the downstream-most base wick layer 210 may be configured to inhibit passage of liquid through the downstream surface 214 while allowing vaporization products to pass through unimpeded. This reduces leakage of liquid vaporization fluid past the heating element of the vaporization device.

Each active material layer 220 is a porous layer that is or includes an active material. The active material layer 220 may be a monolithic or self-sustaining structure bonded to or held in place by the surrounding base wick structures 210. Alternatively, the active material layer 220 may be a non-structural layer of unbonded particles, fibers, flakes or leaves. In a particular embodiment, the active material layer 220 may be a collection of flakes or whole or partial leaves (e.g., tobacco flakes or leaves) that are pressed together to provide a degree of structural integrity. In another particular embodiment, the active material layer 220 may be tobacco paper. In all cases, the active material layer 220 is porous (either as-formed or due to perforation) to allow fluid to flow through the layer. The lateral surfaces of the active material layers 220 (or the entire composite wick 200) may be surrounded by a casing or membrane to maintain structural integrity. Such a casing may be permeable or impermeable and may itself be or include an active material.

In some embodiments, the active material layers 220 may each be or include a wicking material in which an active material is disposed or to which an active material is bonded. The active material layers 220 could each, for example, be similar to the composite wick 100, providing both wicking and active material enhancement. In other embodiments, the base wick layers 210 may be similar to the composite wick 100 with active material dispersed therein.

In embodiments where there are multiple active material layers 220, the characteristics of each layer need not be the same. For example, different layers may have different active materials or may have different amounts of the same active material. They may also have different thicknesses and/or flow-through or wicking properties.

The placement and use of the composite wick 200 is substantially similar to that of the previously described composite wick 100. When placed in a micro-vaporizer device such as the personal vaporizer 10, the composite wick 200 is positioned so that the upstream surface 212 is in contact with the vaporizable fluid in or from a reservoir and the downstream surface 214 is adjacent or in contact with the heating element. The vaporizable fluid is drawn into and through the wick in flow direction F. The porous nature of the relatively thin active material layers 220 allows the passage of the fluid through these layers from base wick layer to base wick layer. In embodiments where the base wick layers 210 are formed from fiber materials, fluid flow across the active material layer 220 may be further enhanced by the fact that the boundaries between the active material layers 220 and the base wick layers 210 are not distinct. The region in the vicinity of such a boundary will actually contain both fiber material from the wick layer and material from the active material layer.

It will be understood that passage through the composite wick 200 necessarily requires fluid to pass through the active material layers 220. As in the previous embodiment, interaction with the active material results in the nature and/or constitution of the fluid changing as it passes through the wick.

As before, when the heating element of the micro-vaporizer device is activated, the a temperature gradient is established within the wick 200 and fluid at or near the downstream surface 214 of the wick 200 is heated to vaporization. The fluid flow characteristics of the base wick layers 210 and the active material layers 220 can be tailored to produce a desired temperature gradient.

Figure 5:
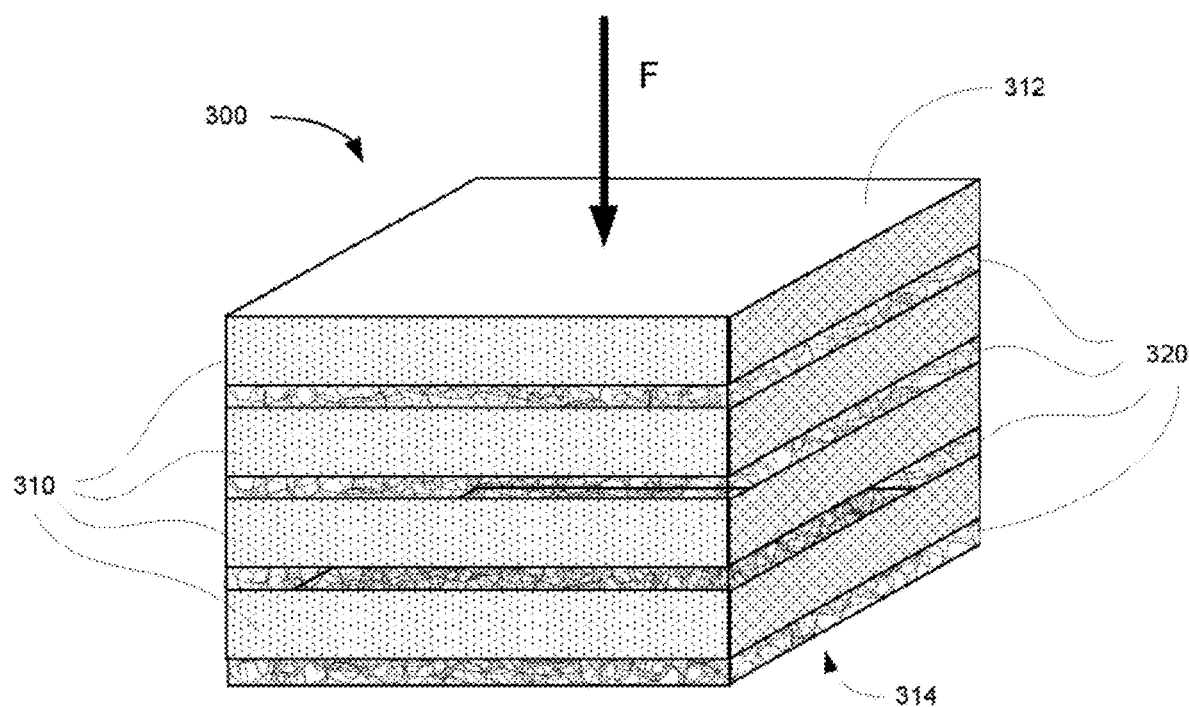
FIG. 5 is a perspective view of a composite wick according to an embodiment of the invention.

As noted above, the base wick layers 210 may be loaded with active material in a fashion similar to the composite wick 100. Such active material can be provided in such a form and disposed in such a way that a portion is exposed at the downstream surface 214 in a manner similar to that described for the composite wick 100'. This provides direct exposure of the active material to the heating element. With reference to FIG. 5, a composite wick 300 according to another embodiment of the invention provides significantly greater exposure of the active material to the heating element when the wick is installed in a micro-vaporizer. The wick 300 is similar to the previous wick 200 in that it has alternating base wick layers 310 and active material layers 320 and in that the upstream-most base wick layer 310 defines the upstream surface 312 of the wick 300. Further, the materials and configurations of the base wick layers 310 and the active material layers 320 are substantially similar to those of the composite wick 200. The composite wick 300 differs, however in that the downstream-most layer is an active material layer 320 that defines the downstream surface 314. This means that, in embodiments where the downstream-most active material layer 320 is formed entirely from an active material, the amount of active material surface area exposed to the heating element is maximized. As before, the fluid flow characteristics of the base wick layers 310 and the active material layers 320 can be tailored to produce a desired temperature gradient. For example, the flow characteristics may be established so as to maintain as much as possible of the active material in the active material layers 320 within the release temperature range of the active material.

While the direct presentation of an active material layer to the heating element as in the use of composite wick 300 may be advantageous for some micro-vaporizer applications (e.g., where the wick is for use in a personal vaporizer and the active material is tobacco), there may be some applications where it would be advantageous to have an exposed active material layer at the upstream surface of the composite wick. In such cases the configuration of the composite wick 300 could be reversed, with an active material layer at the upstream surface and a base wick layer at the downstream surface. In other embodiments, a layered composite wick could have active material layers at both upstream and downstream surfaces.

Figure 6:
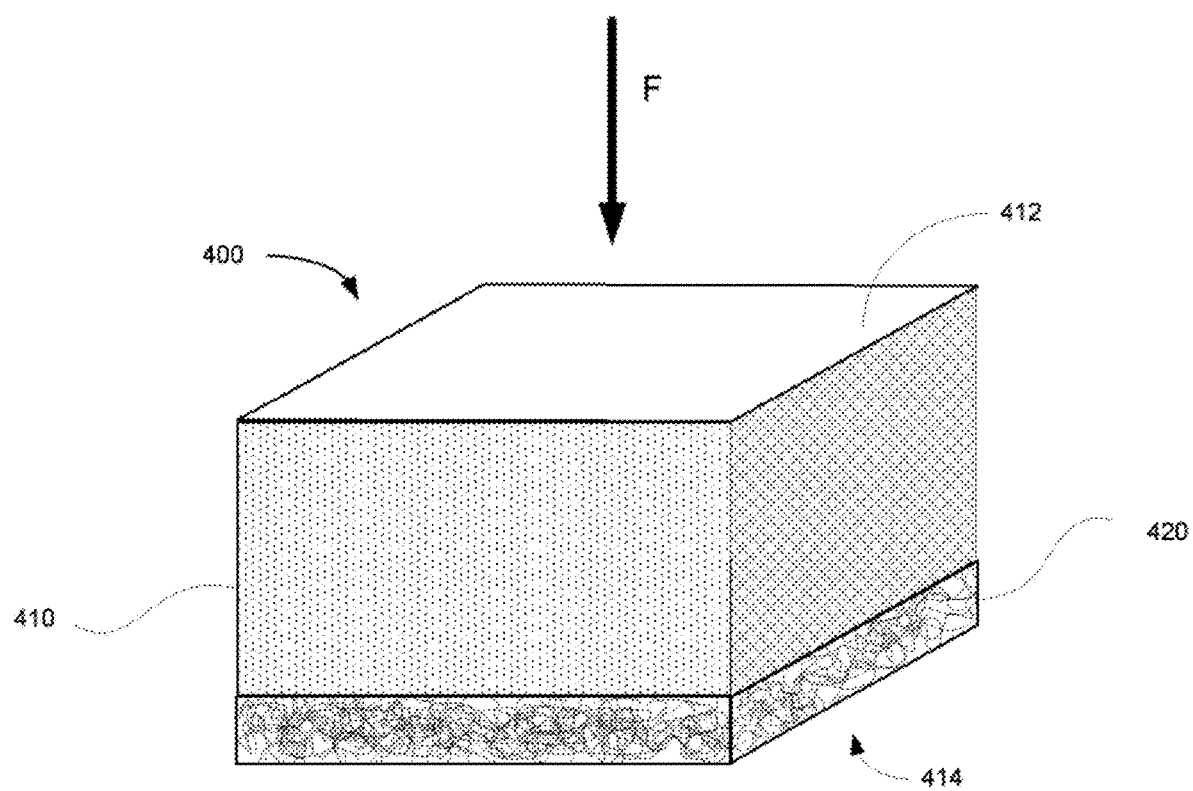
FIG. 6 is a perspective view of a composite wick according to an embodiment of the invention.

With reference to FIG. 6, a composite wick 400 according to yet another embodiment of the invention has a base wick main body 410 defining an upstream surface 412 and an active material layer 420 bonded to or held in abutment with the base wick main body 410 downstream side of the main body 410. The wick main body 410 can have similar materials and configuration to the base wick 110 of the composite wick 100. It can also have active material attached to or disposed within its tortuous passages. The active material layer 420 can be substantially similar to the active material layers of the previously described layered composite wicks 200, 300. Placement of the active material layer 420 at the downstream surface 414 provides similar exposure advantages to those of the composite wick 300 and the fluid and/or vaporization products must pass through the porous active material layer prior to exiting the wick 400 and entering the vaporization chamber. As before, the fluid flow characteristics of the base wick main body 410 and the active material layer 420 can be tailored to produce a desired temperature gradient. For example, the flow characteristics may be established so as to maintain as much as possible of the active material layer 420 within the release temperature range of the active material.

In the wick 400 illustrated in FIG. 6, the active material layer 420 and the downstream surface 414 are positioned opposite the upstream surface 412. It will be understood, however, that the downstream surface could be or include one or more of the lateral surfaces of the wick. In such cases, an active material layer may be positioned on any one or more of the lateral surfaces in addition to or instead of the surface opposite the upstream surface 412. In a particular embodiment, a base wick main body 410 could have an active material layer on each lateral side of the wick (or around the complete circumference if the wick main body 410 is circular). Such laterally-oriented active material layers could also be added to any of the composite wicks described herein.

As was the case with the composite wick 300 configuration, it would also be possible to reverse the position of the active material layer, placing it on the upstream side of the base wick main body.

Figure 7:
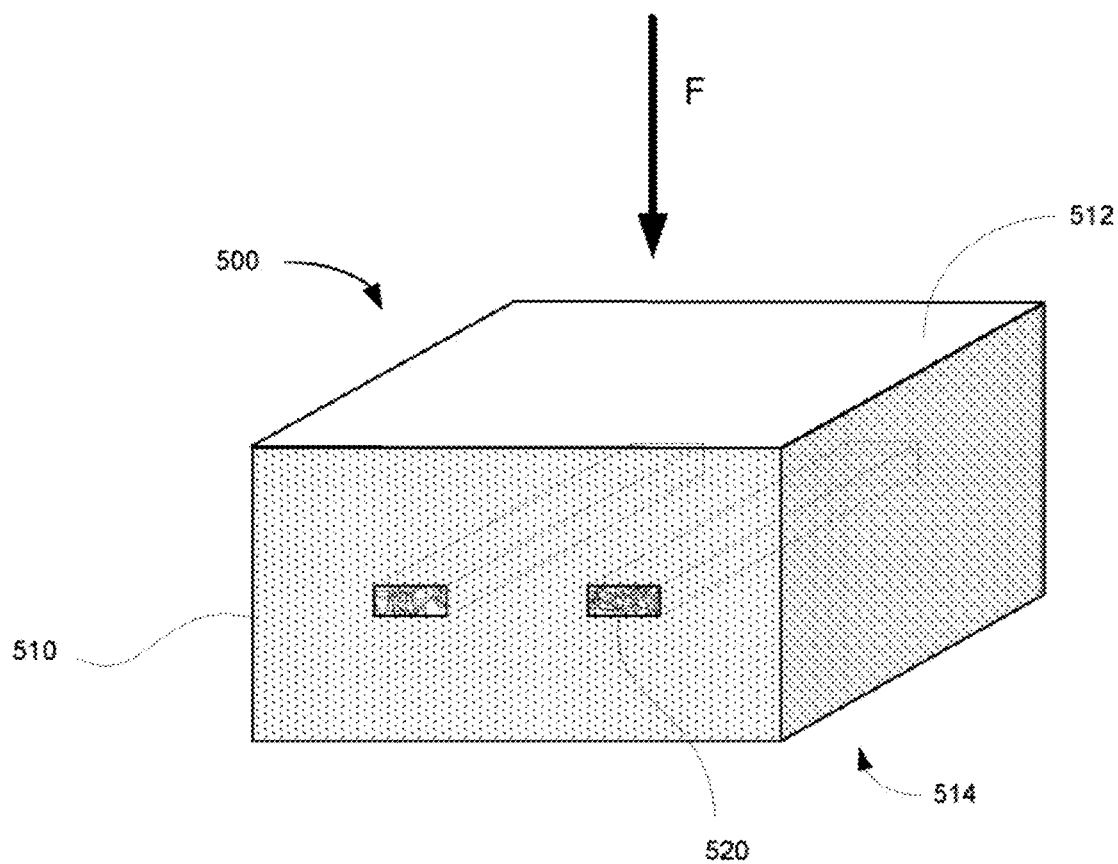
FIG. 7 is a perspective view of a composite wick according to an embodiment of the invention.

With reference to FIG. 7, a composite wick 500 according to yet another embodiment of the invention has a base wick main body 510 defining an upstream surface 512 and a downstream surface 514. The wick main body 510 can have similar materials and configuration to the base wick 110 of the composite wick 100. It can also have active material attached to or disposed within its tortuous passages. The composite wick 500 also has one or more elongate active material bodies 520 embedded within the wick main body. The active material bodies 520 may be in the form of slivers or rods of active material or can be substantially similar to the active material layers of the previously described layered composite wicks 200, 300, but with limited lateral extent. The active material bodies 520 are oriented generally orthogonal to the flow direction F so that wicked fluid can flow around and/or through the active material to maximize interaction between the fluid and the active material. The fluid flow characteristics of the base wick main body 510 can be tailored to produce a desired temperature gradient within the wick 500.

The base wick structures of the above-described composite wick embodiments may have any lateral cross-section including, but not limited to, rectangular (as shown in the figures) or other polygonal shape, circular, elliptical, or free-form. The upstream and downstream surfaces 112, 114 may be substantially planar as shown or may have a degree of uniform curvature or other desired topography.

Figure 8:
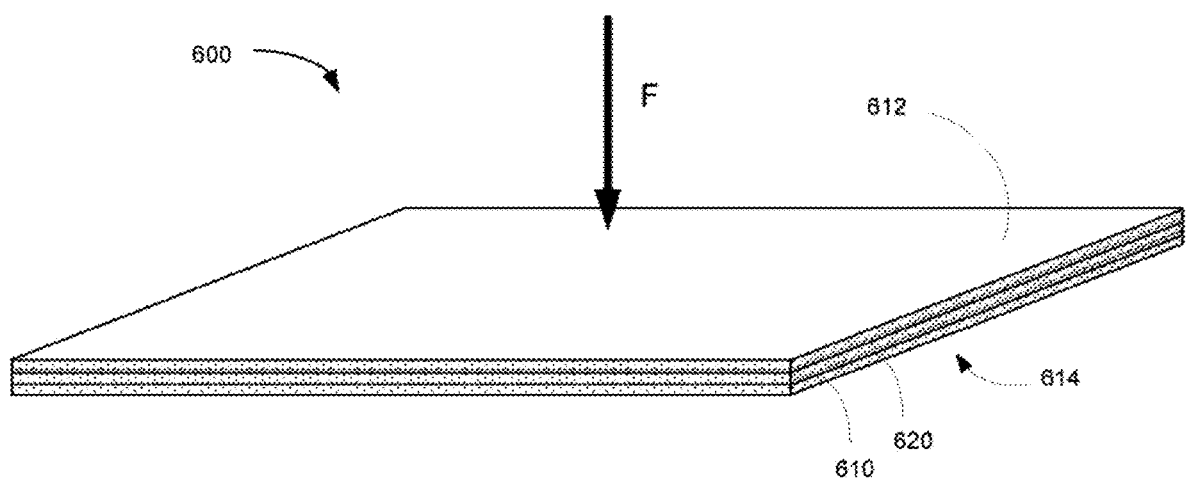
FIG. 8 is a perspective view of a composite wick according to an embodiment of the invention.

The descriptions and illustrations of the foregoing embodiments are presented in the context of a generally planar wick structure with limited lateral extent. It will be understood, however, that any of the foregoing embodiments may be used to provide a generally planar wick sheet having relatively large lateral dimensions relative to the thickness of the wick structure. FIG. 8 illustrates an exemplary composite wick 600 that is in the form of a generally planar sheet. The composite wick 600 is similar in form to the layered composite wick 200 of FIG. 4 with similar base wick layers 610 and active material layers 620. In this embodiment, however, the upstream surface 612 and downstream surface 614 present large areas relative to the cross-sectional are of the wick. This provides for a much higher available area for contact with fluid in the reservoir of a micro-vaporizer and/or for exposure to the micro-vaporizers heating element.

Depending on the wick and active materials and the desired layup of the wick, a composite wick sheet may be formed through weaving, bonding, pressing, or calendering. In some embodiments, the wick sheet may be formed by producing (e.g., by melt-blowing, spun bonding, melt-spinning, or a combination thereof) a loose fiber web which is then passed through a die, pressed or calendered to form a close-packed sheet of fiber. Individual layers of active material can be similarly formed by weaving, bonding, pressing or calendering and then bonded to or pressed with base wick layers to form layered composite wicks. In embodiments where the active material is distributed throughout the base wick material, the active material can be deposited into or bonded to the wick material (e.g., organic or inorganic fibers) prior to the wick material being woven, bonded, pressed, or calendered into a sheet. Sheets may be formed using both batch and continuous manufacturing processes.

The resulting composite wick sheet may then be cut to desired dimensions. The sheet may be cut to produce relatively large sheets like the composite wick 600 or it may be cut to provide multiple composite wicks of smaller dimensions like those shown in FIGS. 2-7. Typical lateral dimensions for a rectangular cross-section composite wick for use in personal vaporizers would be 0.25-1.25 cm by 0.5-2.0 cm. A generally suitable thickness would typically be in a range of 0.1-0.5 cm. A particularly suitable thickness would be in a range of 0.15-0.45 cm and, even more suitably, in a range of 0.25-0.35 cm.

Figure 9:
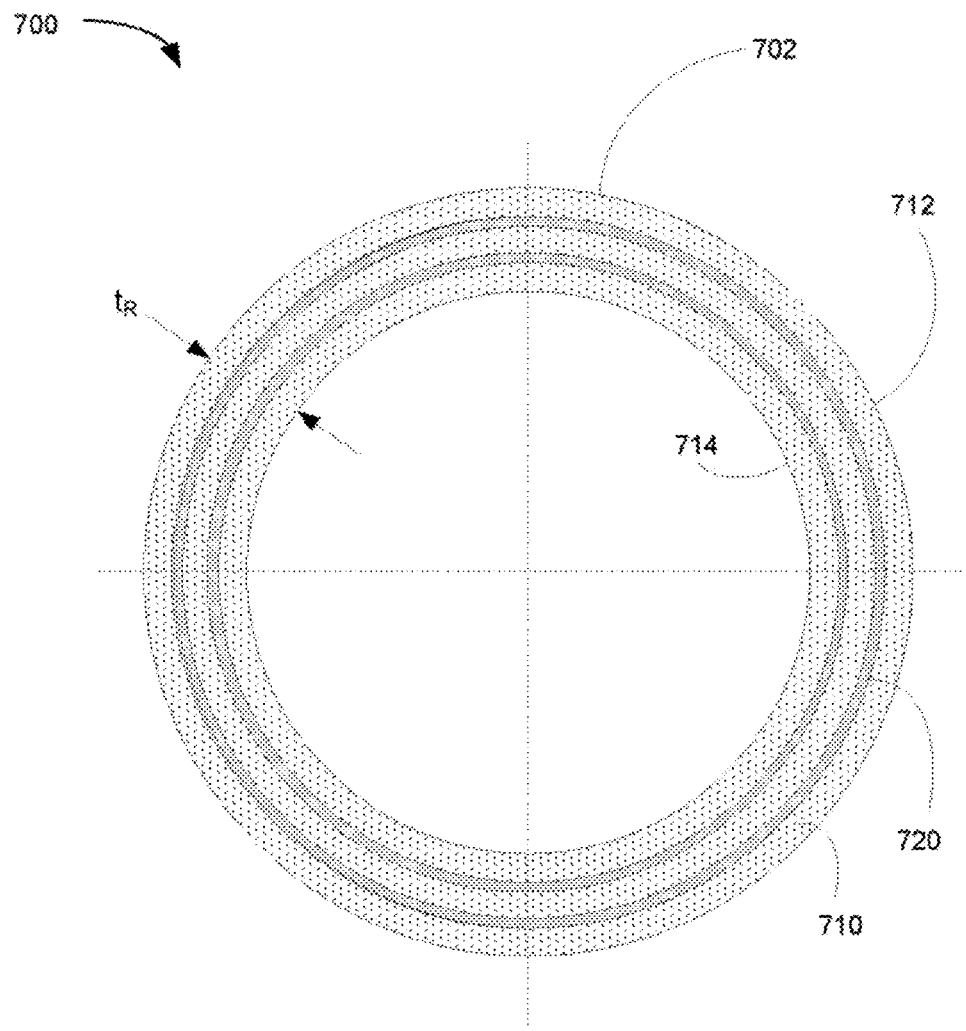
FIG. 9 is an end view of a composite wick according to an embodiment of the invention.

In another embodiment illustrated in FIG. 9, a composite wick 700 according to an embodiment of the invention is formed into an annular cylindrical body 702 having an outer surface 712 and an inner surface 714. The composite wick 700 is configured so that the primary flow direction for wicked fluid is radially through the radial thickness $t_R$ of the body 702. Depending on the configuration of the micro-vaporizer in which the composite wick 700 is to be used, the primary flow direction may be inward or outward. For example, as shown schematically in FIG. 10, a micro-vaporizer may have an annular cylindrical vaporizable fluid reservoir 40' with an outer wall 41' and a centrally located cylindrical heating element 70'. In this exemplary application, the composite wick 700 is placed radially intermediate the reservoir 40' and the heating element 70' so that the outer surface 712 provides an inner boundary for the reservoir 40' and is in contact with fluid in the reservoir 40'. The inner boundary 714 of the composite wick 700 is exposed to the outer surface 71' of the heating element 70'. In this configuration, the primary flow direction through the composite wick 700 will be radially inward. With the vaporization products entering the vaporization chamber 30' surrounding the heating element 70'.

In some embodiments, the inside diameter of the composite wick 700 may be sized to be very close to or even in contact with some or all of the heating element surface 71'. It will be understood that in some instances, the heating element 70' could be configured in forms other than a smooth cylinder so that some areas of the wick inner surface 714 may be closer in proximity to (or in contact with) the heating element 70' than other areas.

Figure 10:
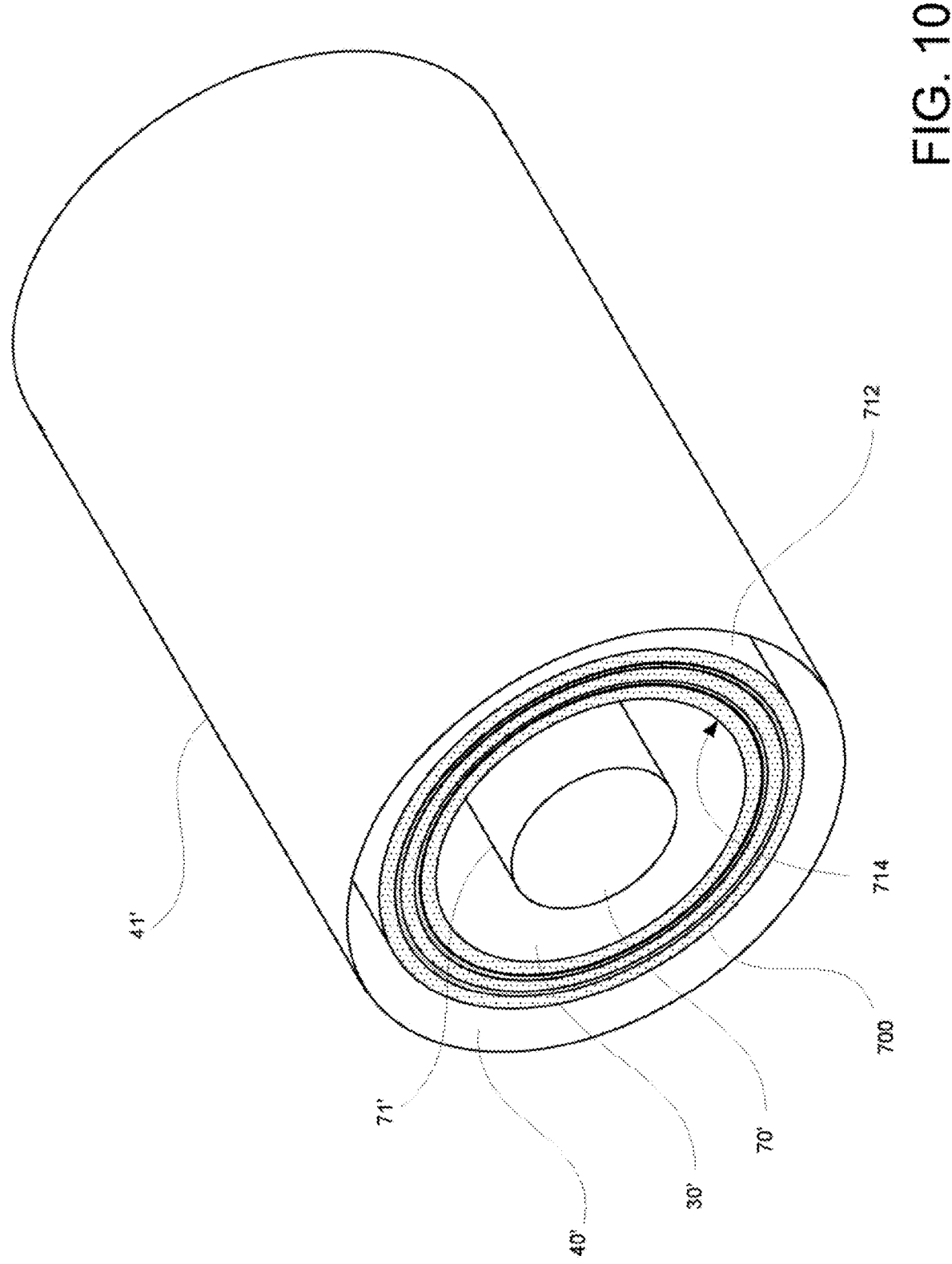
FIG. 10 is a perspective view of a portion of a personal vaporizer including a composite wick according to an embodiment of the invention.

As shown in FIGS. 9 and 10, the composite wick 700 is a layered structure similar to those of the wicks 200, 600 of FIGS. 4 and 8, having a plurality of base wick layers 710 and active material layers 720. It will be understood, however, that similar cylindrical wicks may be formed from any of the previously described composite wick structures. Regardless of their cross-sectional form, any of the annular cylindrical wicks of the invention can initially be formed as sheet-like composite wicks (like the composite wick 600 of FIG. 8), which are than curved into an annular cylinder. This may be accomplished using a cylindrical mandrel or, in some embodiments, directly on a cylindrical casing of the heating element 70'.

Regardless of which surface 712, 714 is the downstream surface, the fluid flow characteristics of the base wick material and, in some cases, the active material used to form the wick 700 can be tailored to produce a desired temperature gradient within the wick adjacent the downstream surface.

In a variation of the previously described embodiment, a composite cylindrical wick 700 may also be adapted for use in a micro-vaporizer having an annular heating element that would at least partially surround the cylindrical wick 700. In such an embodiment, the composite wick 700 would be configured to draw fluid from a central reservoir source toward the outer surface 712, which would be exposed to the heating element. In such an embodiment, the cylindrical wick 700 could be sized for insertion into the annular passage of the heating element.

It will be understood that in any of the composite wicks of the invention, surface areas (e.g., the lateral surface areas of the wicks shown in FIGS. 2-8 or the end areas of the cylindrical wick of FIG. 9) through which fluid flow is not desired may be sealed using a casing or wall. In some instances, flow through such surface areas may be prevented by a wall of the micro-vaporizer structure in which the wick is installed.

Figure 11:
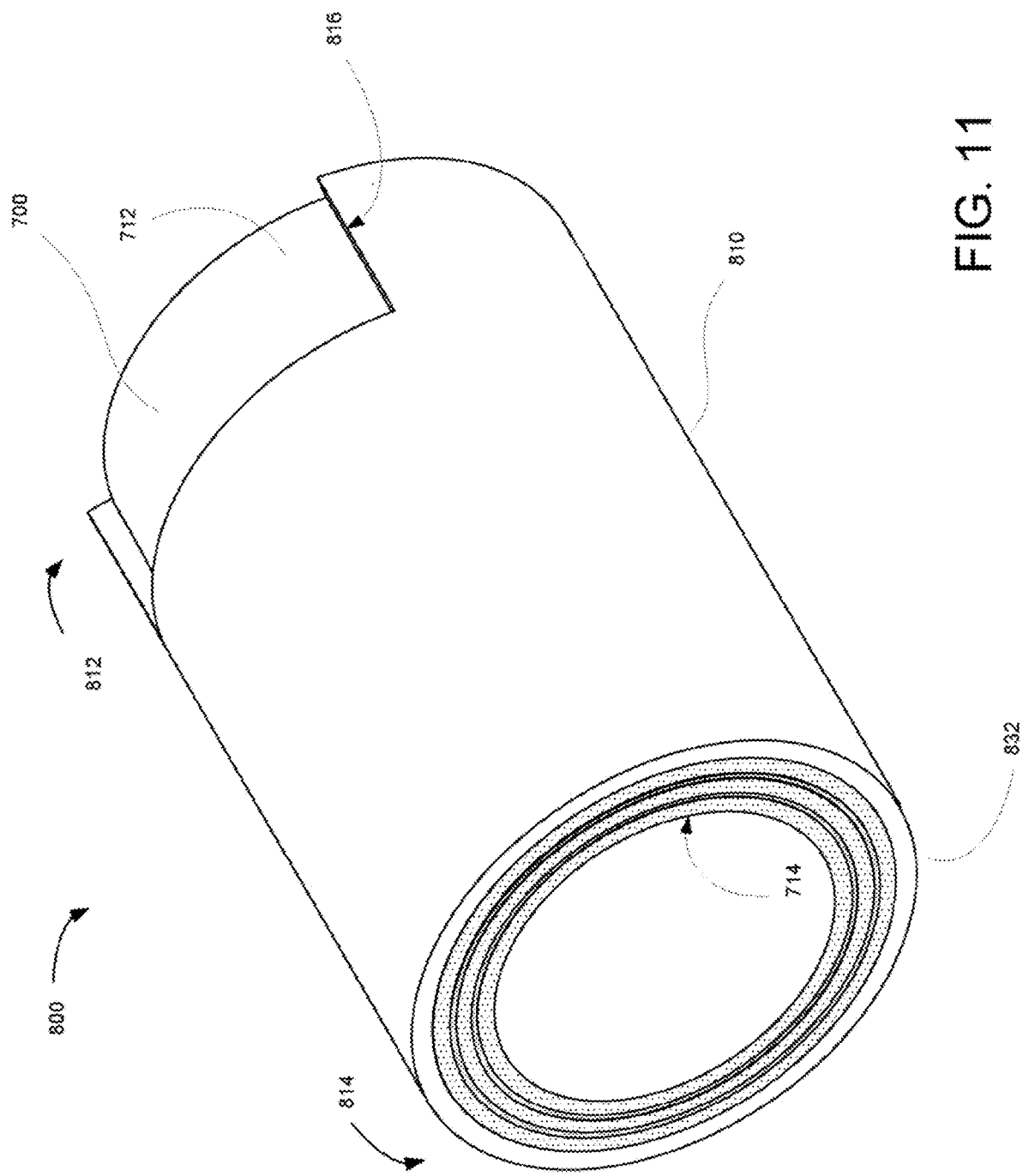
FIG. 11 is a is a perspective view of an encased composite wick according to an embodiment of the invention.

In some applications, it may be advantageous to have a large area of exposure of the downstream surface of the wick to the heating element of a micro-vaporizer, but a relatively small area of exposure of the upstream surface of the wick to the fluid in the micro-vaporizer's fluid reservoir. In such applications, a portion of the upstream wick surface may be shielded from the fluid reservoir by a wall, casing or membrane. FIG. 11 illustrates an embodiment of the invention in which the cylindrical annular composite wick 700 is surrounded by a casing 810 to form a cartridge 800 extending from a first cartridge end 812 to a second cartridge end 814. The cylindrical casing 810 is formed with a notch 816 at the first cartridge end that exposes a portion of the outer surface 712 of the cylindrical composite wick 700. When positioned in a micro-vaporizer having the reservoir and heating element configuration of FIG. 10, the casing 810 provides a wall between the reservoir 40' and the outer surface 712 of the cylindrical composite wick 700. In use, fluid from the reservoir 40' will be drawn into the wick 700 only through the surface area exposed by the notch 816. The fluid will be drawn both inwardly toward the heating element 70' and longitudinally toward the second cartridge end. The structure of the base wick portion of the composite wick 700 may be configured so as to enhance the longitudinal flow characteristics of the wick so as to assure that vaporizable fluid reaches the inner surface 714 along the entire length of the cylindrical wick 700.

Figure 12:
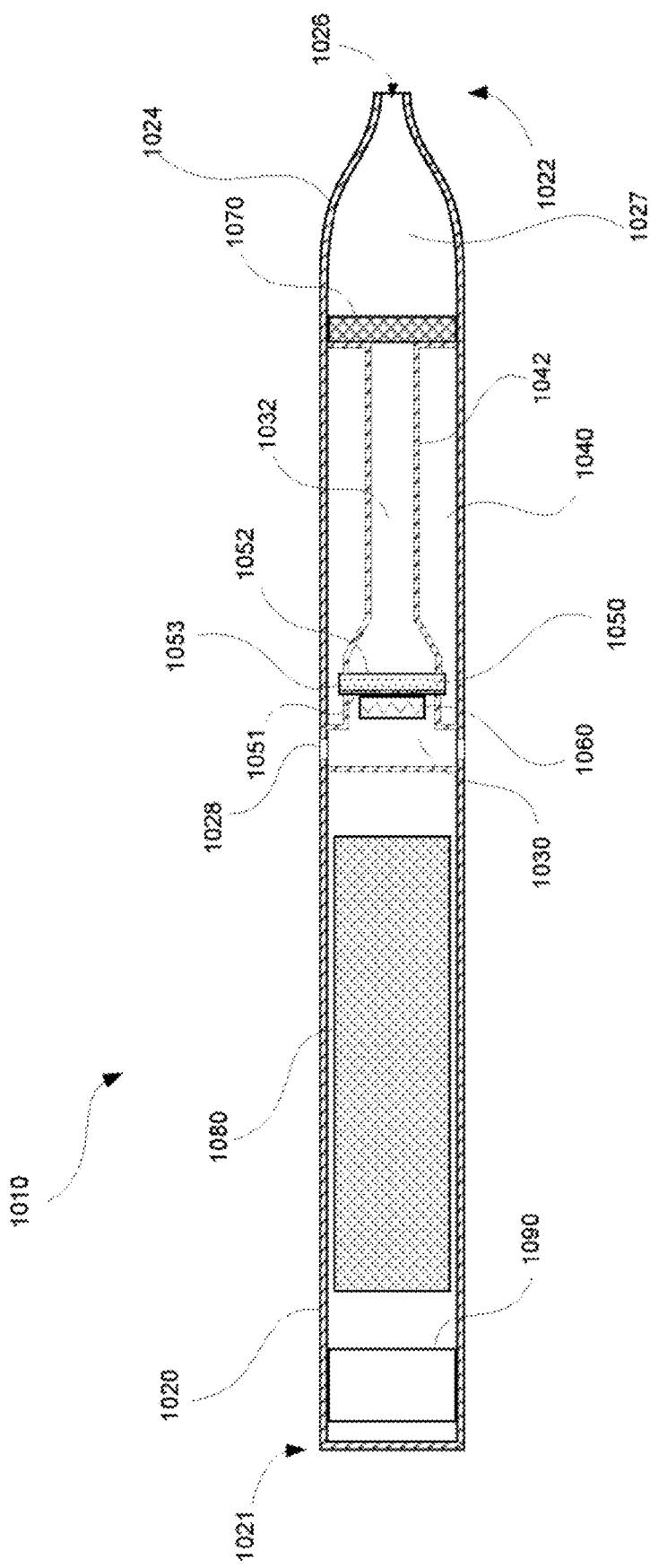
FIG. 12 is a cross-sectional view of a personal vaporizer usable in conjunction with embodiments of the invention.

The composite wicks of the invention may be adapted to virtually any reservoir/heating element configuration. FIG. 12, for example, illustrates a personal vaporizer 1010 similar to the personal vaporizer of FIG. 1 in that it has a cylindrical casing 1020 with a distal end 1021 and a proximal end 1022, a mouthpiece 1024 with an exit passage 1026, a filter 1070, and an exit chamber 1027. The personal vaporizer 1010 also has a battery 1080 and, optionally, a control unit 1090. Like the personal vaporizer 10 of FIG. 1, the personal vaporizer 1010 has one or more air holes 1028 through the casing 1020 to allow air to flow into a vaporization chamber 1030. It differs, however, in that it has a cylindrical fluid reservoir 1040 that surrounds a portion of the vaporization chamber 1030 and the heating element 1060. The heating element 1060 may advantageously be, for example, a coil or circular mesh resistance element. The heating element 1060 is positioned at or near the proximal end of the vaporization chamber 1030, which is in fluid communication with a chimney 1032 bounded by the inner wall 1042 of the reservoir. The chimney 1032 provides a conduit through which air and vaporization products pass from the vaporization chamber 1030 to the filter 1070 and exit chamber 1027.

To supply fluid for vaporization by the heating element 1060, the personal vaporizer 1010 is provided with a disc-like wick 1050 having distal, proximal and circumferential surfaces 1051, 1052, 1053. The wick 1050 is centered on the longitudinal axis of the personal vaporizer 1010 so that the wick's distal surface 1051 is adjacent or in contact with the heating element 1060. The wick 1050 is sized so that it extends outward to and through a circumferential opening 1041 in the inner wall 1042 of the fluid reservoir 1040. The wick 1050 is configured so that fluid in the reservoir 1040 is drawn into the wick 1050 through the circumferential surface 1056 and/or through portions of the distal and proximal surfaces 1051, 1052 adjacent the circumferential surface 1056. The wick 1050 is further configured so that the vaporizable fluid is drawn inwardly toward the longitudinal axis of the personal vaporizer 1010 and proximally toward the proximal surface 1052 where it is exposed to heat from the heating element 1060 and vaporized.

Figure 13:
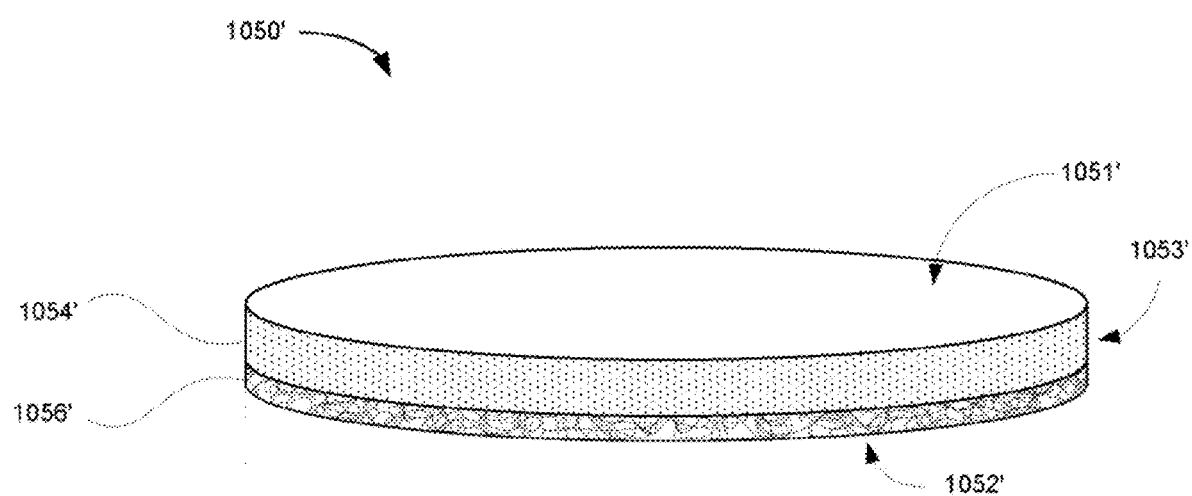
FIG. 13 is a perspective view of a composite wick according to an embodiment of the invention.

Any of the composite wick configurations discussed above can be used in the disc-like wick 1050 of the personal vaporizer 1010. FIG. 13 illustrates an exemplary composite wick 1050' having similar characteristics to the wick 400 of FIG. 6. The composite wick 1050' has a base wick main body 1054' that defines the proximal surface 1052' and an active material layer 1056' bonded to or held in abutment with the base wick main body 1054' that defines the distal surface 1051'. As previously described, such a configuration positions the active material for direct exposure to or contact with the heating element 1060. The wick main body 1054' and the active material layer 1056' are both formed as thin (i.e., disc-like) cylindrical elements and collectively define the circumferential surface 1053'.

As previously noted, the various composite wick embodiments described above can be used in any micro-vaporizer requiring transport of vaporizable fluid from a reservoir to another location where it is heated to vaporization. The wicks of the invention are particularly suited, however to use in personal vaporizers. Many users turn to these devices as alternatives to or replacements for burning tobacco products such as cigarettes, cigars, pipes, etc. For such users, the ideal replacement would be one that mimics the burning tobacco experience to the greatest extent.

Heretofore, personal vaporizers have been limited in their ability to mimic the burning tobacco experience. The typical vaporizable fluid used in these devices may include nicotine and a flavorant intended to mimic the taste of a tobacco product, but it does not actually include tobacco. The composite wicks of the invention provide the ability to impart tobacco characteristics to the vaporizable fluid and to even provide the ability to mimic the smoky burning sensation of a cigarette or cigar. This is accomplished by using real tobacco as the active material in the wick used to transport the vaporizable fluid. In this approach, the wick acts as both a liquid transport device and a flavoring agent. As has been discussed, the wicks may also provide a mechanism for directly exposing portions of tobacco material to the heating element, which produces a small degree of burning, the products of which are mixed with the vaporization products from the liquid. The combined products are then mixed with the air being drawn through the device and inhaled by the user.

While the foregoing illustrates and describes exemplary embodiments of this invention, it is to be understood that the invention is not limited to the construction disclosed herein. The invention can be embodied in other specific forms without departing from the spirit or essential attributes.

What is claimed is:

1. A composite wick for use in a vaporizer having a vaporizer body in which is disposed a vaporizable fluid reservoir and a vaporization chamber with a heating element at least partially disposed therein, the composite wick comprising:
   a wick body terminating at upstream and downstream base surfaces and being positionable within the vaporizer body so that the upstream base surface is in fluid communication with the vaporizable fluid reservoir and the downstream base surface is disposed within the vaporization chamber in opposition to a surface of the heating element, the wick body comprising:
      at least one base wick structure having a plurality of tortuous passages that collectively provide a capillary effect to draw vaporizable fluid from the vaporizable fluid reservoir and transport it toward the downstream base surface, and
      an active material positioned so that vaporizable fluid drawn through the wick body contacts and interacts with the active material, the active material being or comprising a flavor-inducing element that is configured to add flavor to the vaporized fluid, the active material having a release temperature of the active material being a temperature at or above which the active material begins to decompose or off-gas,
   wherein the active material has a release temperature at or above which the active material releases an agent, and
   wherein the active material is arranged within the wick body so that at least a majority of the active material is maintained within its release temperature when the heating element is activated.

2. A composite wick according to claim 1 wherein an entry of the vaporizable fluid into the wick body from the vaporizable fluid reservoir is confined to a passage through the upstream base surface.

3. A composite wick according to claim 1 wherein an exit of the vaporizable fluid from the wick body into the vaporization chamber is confined to a passage through the downstream base surface.

4. A composite wick according to claim 1 wherein the composite wick further comprises:
   an impermeable casing surrounding all surface area of the wick body intermediate the upstream and downstream base surfaces.

5. A composite wick according to claim 1 wherein the at least one base wick structure comprises a plurality of organic or inorganic fibers.

6. A composite wick according to claim 5 wherein the at least one base wick structure is formed as a compressed non-woven web of fibers.

7. A composite wick according to claim 5 wherein the plurality of fibers are bonded to one another at spaced apart points of contact to form a self-sustaining bonded fiber structure.

8. A composite wick according to claim 1 wherein the active material is in the form of at least one of the set consisting of particles, powder, and flakes dispersed within the at least one base wick structure.

9. A composite wick according to claim 1 wherein the active material is provided in the form of generally planar flakes dispersed within the at least one base wick structure so that the flakes are generally parallel to the upstream and downstream base surfaces.

10. A composite wick according to claim 1 wherein the wick body is formed as a plurality of layers in which each of the at least one base wick structure and each of at least one porous active material layer comprising the active material are positioned in an alternating layer sequence.

11. A composite wick according to claim 10 wherein each of the at least one porous active material layer comprises one of the set consisting of a self-sustaining structure having active material dispersed therein and a self-sustaining structure formed from active material.

12. A composite wick according to claim 10 wherein each of the at least one porous active material layer comprises compressed, unbonded active material.

13. A composite wick according to claim 10 wherein the downstream base surface is defined by one of the at least one porous active material layer.

14. A composite wick according to claim 1 wherein the active material is tobacco.

15. A composite wick according to claim 1 wherein the active material is one of the set consisting of whole tobacco leaves, shredded tobacco leaves, crushed and dried tobacco flakes, slivers of dried tobacco leaves, and shavings from dried tobacco leaves.

16. A composite wick according to claim 1 wherein the active material has a combustion temperature and the at least one base wick structure is configured to control fluid flow so as to prevent temperatures within the active material from exceeding the combustion temperature when the wick body is disposed within the vaporizer and the heating element is activated.

17. A composite wick for use in a vaporizer having a vaporizer body in which is disposed a vaporizable fluid reservoir and a vaporization chamber with a heating element at least partially disposed therein, the composite wick comprising:
a wick body terminating at upstream and downstream base surfaces, and being positionable within the vaporizer body so that the upstream base surface is in fluid communication with the vaporizable fluid reservoir and the downstream base surface is disposed within the vaporization chamber in opposition to a surface of the heating element, the wick body comprising:
a base wick material having a plurality of tortuous passages that collectively provide a capillary effect to draw vaporizable fluid from the vaporizable fluid reservoir and transport it toward the downstream base surface; and
at least one porous active material comprising a flavor-inducing element that is configured to add flavor to the vaporized fluid,
wherein the at least one porous active material has a release temperature at or above which the at least one porous active material releases an agent,
wherein the wick body comprises a release temperature region that is configured to be heated to at least the release temperature of the at least one porous active material by the heating element when the wick body is positioned within the vaporizer body and the heating element is activated, and
wherein a majority of the at least one porous active material is located within the release temperature region of the wick body.

18. A composite wick according to claim 17 wherein the wick body comprises at least one base wick layer and at least one porous active material layer.

19. A composite wick according to claim 17 wherein the downstream surface is defined by one of the at least one porous active material layer.

20. A composite wick according to claim 18, wherein the at least one porous active material is absent from the at least one base wick layer.

21. The composite wick of claim 1, wherein the active material is or comprises at least one of the set consisting of a flavorant, a fragrance, a plant material, and a medication.

22. A composite wick according to claim 1, wherein the wick body is in the form of a cylinder or prism.

23. The composite wick of claim 17, wherein the at least one porous active material is or comprises at least one of the set consisting of a flavorant, a fragrance, a plant material, and a medication.

24. A composite wick according to claim 17, wherein the wick body is in the form of a cylinder or prism.

25. The composite wick of claim 1, wherein the active material is arranged within the wick body so that all of the active material is maintained within its release temperature when the heating element is activated.

26. The composite wick of claim 17, wherein all of the at least one porous active material is located within the release temperature region of the wick body.

* * * * *